United States Patent [19]

Peel et al.

[11] Patent Number: 4,779,626
[45] Date of Patent: Oct. 25, 1988

[54] METHOD AND APPARATUS FOR COMPENSATING FOR TRANSDUCER POSITION IN BLOOD PRESSURE MONITORING SYSTEM

[75] Inventors: Harry H. Peel; James M. Burkes, both of San Antonio, Tex.

[73] Assignee: Colin Electronics Co., Ltd., Komak, Japan

[21] Appl. No.: 905,697

[22] Filed: Sep. 9, 1986

[51] Int. Cl.$^4$ ............................................... A61B 5/02
[52] U.S. Cl. .................................. 128/675; 128/673; 128/748; 73/716
[58] Field of Search .............................. 128/672–675, 128/748; 73/716–722

[56] References Cited

U.S. PATENT DOCUMENTS 4,240,294 12/1980 Grande ........................... 128/673 X
4,576,035 3/1986 Hooven et al. .................. 128/748 X

OTHER PUBLICATIONS

Corbett et al.; "A Self-Leveling Central Venous Electromanometer", *Med. and Biol. Engr.*, vol. 12, No. 3, 11-1974, p. 366.

*Primary Examiner*—William E. Kamm
*Assistant Examiner*—Angela D. Sykes
*Attorney, Agent, or Firm*—Hamilton, Smith & Clarkson

[57] ABSTRACT

A method and apparatus for ensuring accurate measurement of blood pressure regardless of the position of the sensing transducer relative to the position of the patient's heart. The method and apparatus provides a hydrostatic balancing system in which a column of fluid is used to offset the hydrostatic pressure created by the corresponding column of blood contained in the blood vessel in the limb upon which the measurement is being taken. A flexible tube is routed along the patient's limb with one end being positioned at heart level and the other end terminating at the occlusion cuff which supports the pressure sensing transducer. The tube is filled with fluid and is connected to a fluid reservoir chamber located at approximately the same level as the patient's heart. The hydrostatic pressure created by the fluid in the tube effectively balances the corresponding hydrostatic pressure created by the blood in the blood vessel. At the cuff end of the tube, a differential pressure transducer senses the difference between the cuff pressure and that generated by the fluid column of the pressure compensation system. This signal, after appropriate scaling, can be used in conjunction with oscillometric signal processing software to provide an accurate representation of the patient's actual blood pressure.

20 Claims, 4 Drawing Sheets

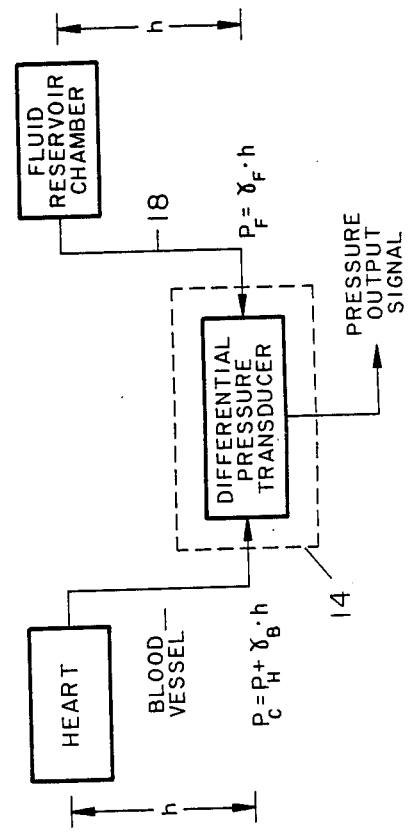
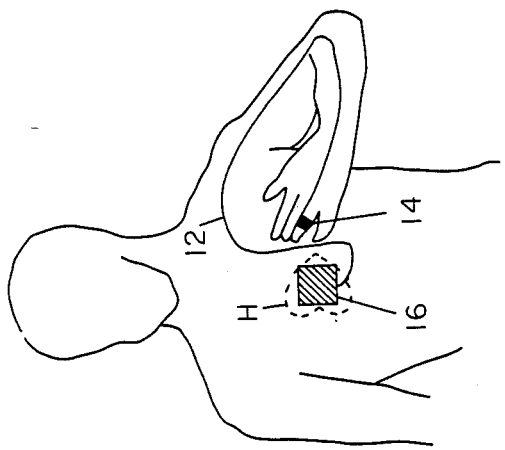
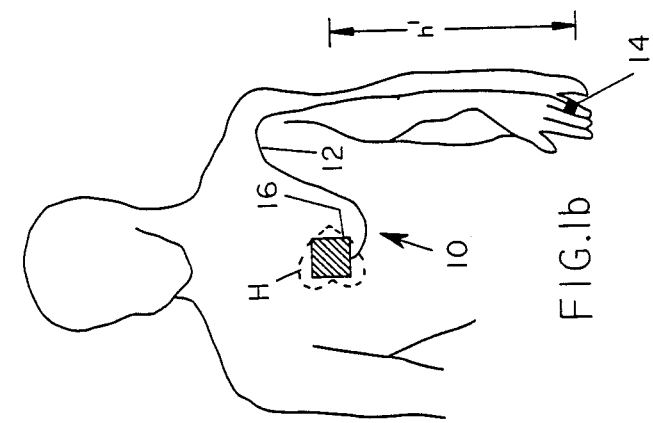
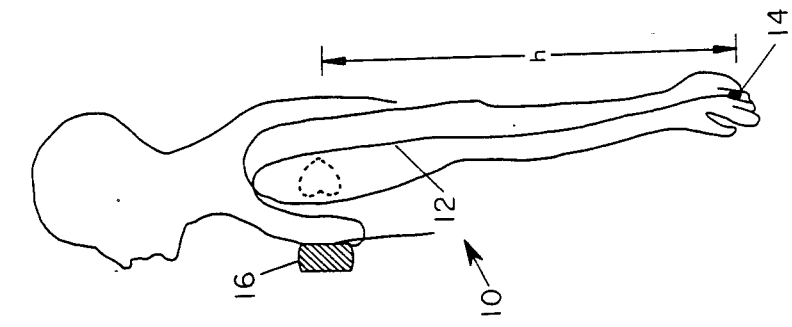

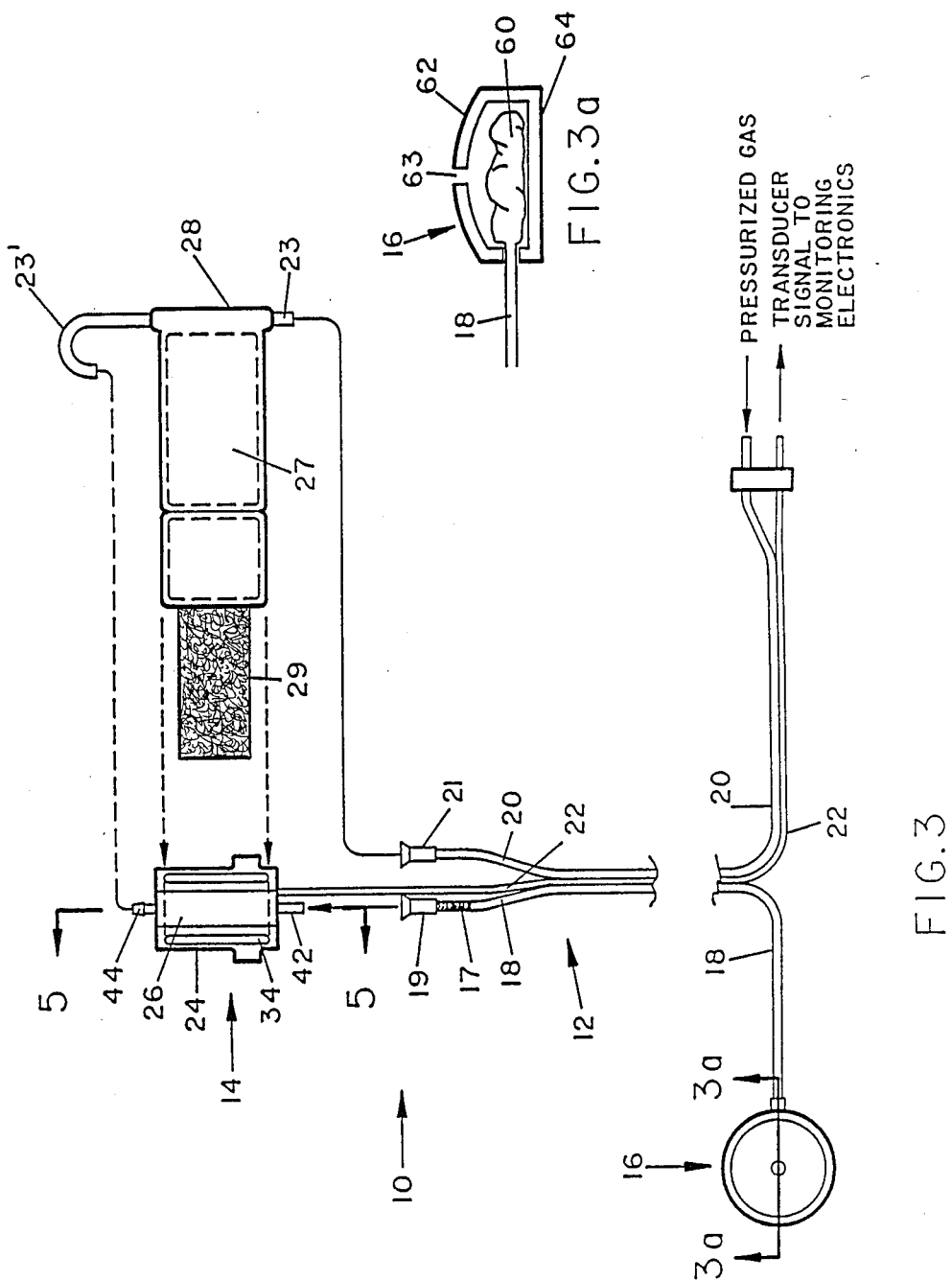

METHOD AND APPARATUS FOR COMPENSATING FOR TRANSDUCER POSITION IN BLOOD PRESSURE MONITORING SYSTEM

FIELD OF THE INVENTION

The present invention is related generally to the field of transducers used in connection with blood pressure monitoring equipment. More specificilly, the present invention provides a method and apparatus for ensuring accurate measurement of blood pressure regardless of the position of the transducer relative to the position of the patient's heart.

BACKGROUND

In many cases, it is desirable for a doctor to be able to monitor a patient's blood pressure over long periods of time. Numerous blood pressure monitoring systems have been developed to provide automatic measurement of the patient's blood pressure at predetermined time intervals. In general, these monitoring systems comprise a transducer which measures pressure variations in a pressurized cuff attached to the patient's arm or flnger. The output from the transducer is processed by a computer algorithm to obtain an indication of the patient's blood pressure.

The blood pressure measured by the transducer using a conventional monitoring system may fluctuate signiflcantly due to a number of physiological and environmental factors. For example, respiration and physical movement of the patient may create motion artifacts and other spurious signals which must be filtered from the transducer output in order to obtain an accurate representation of the patient's blood pressure. Most monitoring systems incorporate sophisticated algorithms to remove these undesired signals and thus ensure the integrity of the blood pressure reading.

In addition to undesired signals such as those discussed above, an additional error can be introduced by pressure differentials which are related to the position of the limb to which the transducer is attached. This error is related to a hydrostatic pressure differential between the blood in the heart and the column of blood in the blood vessel where the pressure measurement is being made.

The importance of correcting for this hydrostatic pressure error depends on the reason for taking the patient's blood pressure and on the situation in which the measurement is being made. As a general principle, the preferred blood pressure measurement is the central aortic systolic and diastolic pressure. However, it is not possible to measure central aortic pressure by indirect measurement techniques, such as those utilizing a transducer attached to the patient's limb. The blood pressure measured in the patient's limb is different from the central aortic pressure because of pulse pressure differentials created by the peripheral arteries. Such pressure differentials are especially prevalent in blood pressure measurements made in the lower arm and the legs.

The pressure differentials related to indirect blood pressure measurement are well understood and the error caused by these differentials are simply factored into the blood pressure measurement. The errors related to hydrostatic pressure differentials, however, can cause significant difflculties in certain diagnostic procedures. In particular, such errors are important in situations where changes in the mean blood pressure are important to obtain a correct diagnosis.

In some situations, such as monitoring a patient in the operating room, it is important to monitor only significant changes in the patient's blood pressure. In other cases, however, it is important that the actual blood pressure be monitored. For example, in the diagnosis of hypertension, the patient's actual blood pressure is monitored over a long period of time. The data obtained during this measurement period are compared to the blood pressures contained in a data base representative of a large population. The actual blood pressure measurements used in this diagnosis are normally taken while the patient is relaxed and sitting or lying on his back with the cuff at heart level. If the position of the pressure transducer relative to the heart is changed during the series of measurements, a hydrostatic pressure of more than 10 mm of mercury can be created. Such a pressure differential is significant enough to cause an error in the diagnosis.

Prior automatic blood pressure monitoring systems have not incorporated a means for compensating for the error caused by the position of the transducer. It is important, therefore, that an effective blood pressure monitoring system be provided which can compensate for the hydrostatic pressure differential related to changes in the position of the transducer relative to the position of the patient's heart.

SUMMARY OF THE INVENTION

The method and apparatus of the present invention overcomes the above-mentioned difficulties and the shortcomings of previous blood pressure monitoring systems by providing an effective compensation system for ensuring accurate measurement of blood pressure regardless of the position of the sensing transducer relative to the position of the patient's heart. In the broadest sense, the invention compensation method and apparatus provides a hydrostatic balancing system in which a column of fluid is used to offset the hydrostatic pressure created by the corresponding column of blood contained in the blood vessel from which the measurement is being taken.

The compensation system comprises a flexible tube which is routed along the patient's limb with one end being positioned at heart level and the other end terminating at the pressure sensing transducer. The tube is fllled with fluid and is connected to a fluid reservoir chamber located at approximately the same level as the patient's heart. Ideally, the fluid contained in the chamber and the tube should have approximately the same density as blood to ensure that the hydrostatic pressure in the tube effectively balances the corresponding hydrostatic pressure created by the blood in the blood vessel. At the cuff end of the tube, a differential pressure transducer senses the difference between the cuff pressure and that generated by the fluid column of the pressure compensation system. This signal, after appropriate scaling, can be used in conjunction with oscillometric signal processing software to provide an accurate representation of the patient's actual blood pressure.

The invention compensation system can easily be calibrated to compensate for drift in the zero-offset signal of the pressure sensing transducer in order to ensure accurate readings over an extended period of time. The desired calibration is accomplished by periodically moving the pressure transducer to the same level as the fluid reservoir chamber. With the transducer in this position, the hydrostatic pressure differential will be equal to zero and the system's electronic circuitry can be adjusted to compensate for transducer drift.

BRIEF DESCRIPTION OF THE DRAWINGS

FIG. 1a is an elevated side view of the transducer position compensation system of the present invention attached to a patient.

FIG. 1b is an elevated perspective view of the transducer position compensation system of the present invention attached to a patient.

FIG. 1c is a perspective front view of the transducer position compensation system of the present invention attached to a patient with the sensor assembly at the same level as the reservoir chamber to allow calibration of the pressure transducer.

FIG. 2 is a block diagram of the transducer position compensation system of the present invention.

FIG. 3 is an exploded view of the invention compensation system showing the interconnection of the major system components.

FIG. 3a is cross-sectional side view of the fluid reservoir chamber taken along section lines 3a–3a of FIG. 3.

DETAILED DESCRIPTION OF THE PREFERRED EMBODIMENT

Figure 4B:
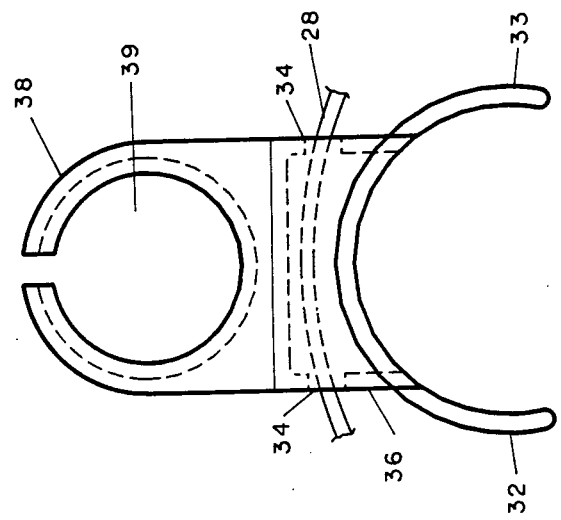
FIG. 4b is an elevated front view of the finger mounting bracket for attaching the sensor assembly to a patient's finger.

Referring to the drawings in more detail and to FIGS. 1a and 1b in particular, the transducer position compensation system 10 of the present invention is shown attached to a patient for use in conjunction with conventional blood pressure monitoring equipment. The compensation system includes a tube assembly 12 which is routed along a limb, such as the patient's arm. The tube assembly 12 comprises a flexible, fluid-filled tube 18 which provides a hydrostatic offsetting pressure in a manner described in greater detail below. The tube assembly also includes a pneumatic line for providing pressurized gas to the occlusion cuff and an electronic line for transmitting the output of the transducer to the monitoring electronics. As can be seen in FIGS. 1a and 1b, one end of the tube assembly is positioned at approximately the same level as the patient's heart H. The other end of the tube assembly 12 is connected to a sensor assembly 14, which is attached to the patient's finger. The fluid reservoir 16, which is attached to the patient at approximately the level of the heart H, absorbs excess fluid and provides additional fluid, as needed, to moderate the fluid pressure in the tube 18.

The general functional features of the transducer position compensation system 10 can be seen by referring to FIG. 1a and the block diagram of FIG. 2. With the patient's arm in the extended position shown in FIG. 1a, the sensor assembly 14 attached to the patient's finger will be separated from the patient's heart by a distance h. In the absence of the position compensation system, the pressure sensed by the transducer in the sensor assembly 14 would be:

$$P_C = P_H + \gamma_B \cdot H \quad (1),$$

where $P_C$ is the pressure in the occlusion cuff attached to the patient's finger, $P_H$ is the blood pressure at the heart, and $\gamma_B$ is the density of blood. As was discussed above, the hydrostatic pressure, $\gamma_B \cdot h$, resulting from the column of blood in the patient's arm causes an error in the measurement of the patient's actual blood pressure. The fluid contained in the tube 18 of the compensation system provides an offsetting pressure, $P_F = \gamma_F \cdot h$, where $\gamma_F$ is the density of the fluid in the tube 18. The pressure differential, $\Delta P$, at the transducer can be calculated substituting the fluid pressure, $P_F$, into equation (1). Thus it can be seen that:

$$\Delta P = P_C - P_F = P_H + (\gamma_B - \gamma_F) \cdot h \quad (2)$$

Referring to eq. (2), it can be seen that the pressure sensed by the transducer will be equal to the pressure at the heart, $P_H$, when the density of the fluid contained in the tube 18 is equal to the density of the blood in the blood vessel in the patient's limb. Under ideal operating conditions, the desired hydrostatic pressure offset could be achieved by simply filling a closed tube of sufficient length with a fluid having the same density as blood. For example, a fluid-filled tube of length h would provide the desired hydrostatic offsetting pressure if the patient's arm were maintained in the position shown in FIG. 1a. Movement of the arm to the position shown in FIG. 1b, however, would cause the tube 18 to compress slightly, thus creating a non-hydrostatic pressure component which would be sensed by the transducer in the sensor assembly 14. Other non-hydrostatic pressure components can be created by environmental factors such as changes in the temperature of the fluid in the tube 18.

In order to maintain the desired hydrostatic pressure offset, the system must be able to compensate for non-hydrostatic pressure components such as those discussed above. In the preferred embodiment of the invention, this compensation is provided by the fluid reservoir chamber 16. The reservoir chamber 16 comprises a fluid-filled bag which is infinitely compliant over the range of pressure and volume changes resulting from physical and environmental factors discussed above. In the preferred embodiment, the reservoir chamber 16 is capable of absorbing up to 25% of the volume of the fluid contained in the tube 18 to maintain a constant hydrostatic reference pressure at the sensor assembly 14. The details relating to the fluid reservoir chamber 16 will be discussed further below.

In the preferred embodiment of the compensation system, a portion of the fluid tube 18 is filled with a plurality of small particles of silica sand 17, shown in FIG. 3. These particles serve as a low pass mechanical filter which removes undesired transient pressure signals. Particles having a diameter of 0.025 inch have been found to provide excellent filtering characteristics. In the preferred embodiment, a column of particles between one and two inches in length is retained in the fluid-filled tube 18 at the approximate location shown in FIG. 3. As an alternative, the desired filtering characteristics can be provided by placing a plug of fibrous material or sintered metal in the tube 18 at the point shown for the particles 17 in FIG. 3.

In addition to the non-hydrostatic pressure errors discussed above, an additional error can be introduced by drift in the zero-offset of the output signal of the pressure transducer contained in the sensor assembly 14. The position compensation system of the present invention can be calibrated to account for transducer signal drift by periodically moving the sensor assembly 14 to the same level as the fluid reservoir 16, as shown in FIG. 1c, so that the distance h will be equal to zero. With the sensor assembly in this position the system can be calibrated to define a zero pressure reading for the transducer.

Figure 4A:
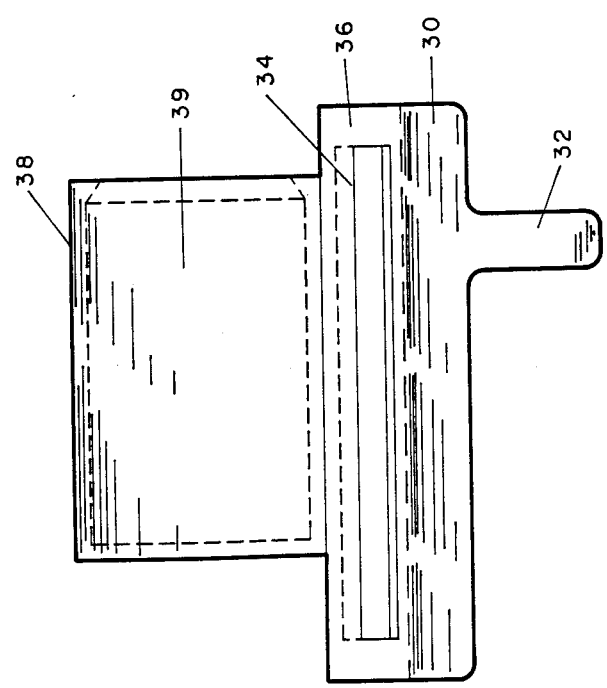
FIG. 4a is an elevated side view of the finger mounting bracket for attaching the sensor assembly to a patient's finger.
Figure 5:
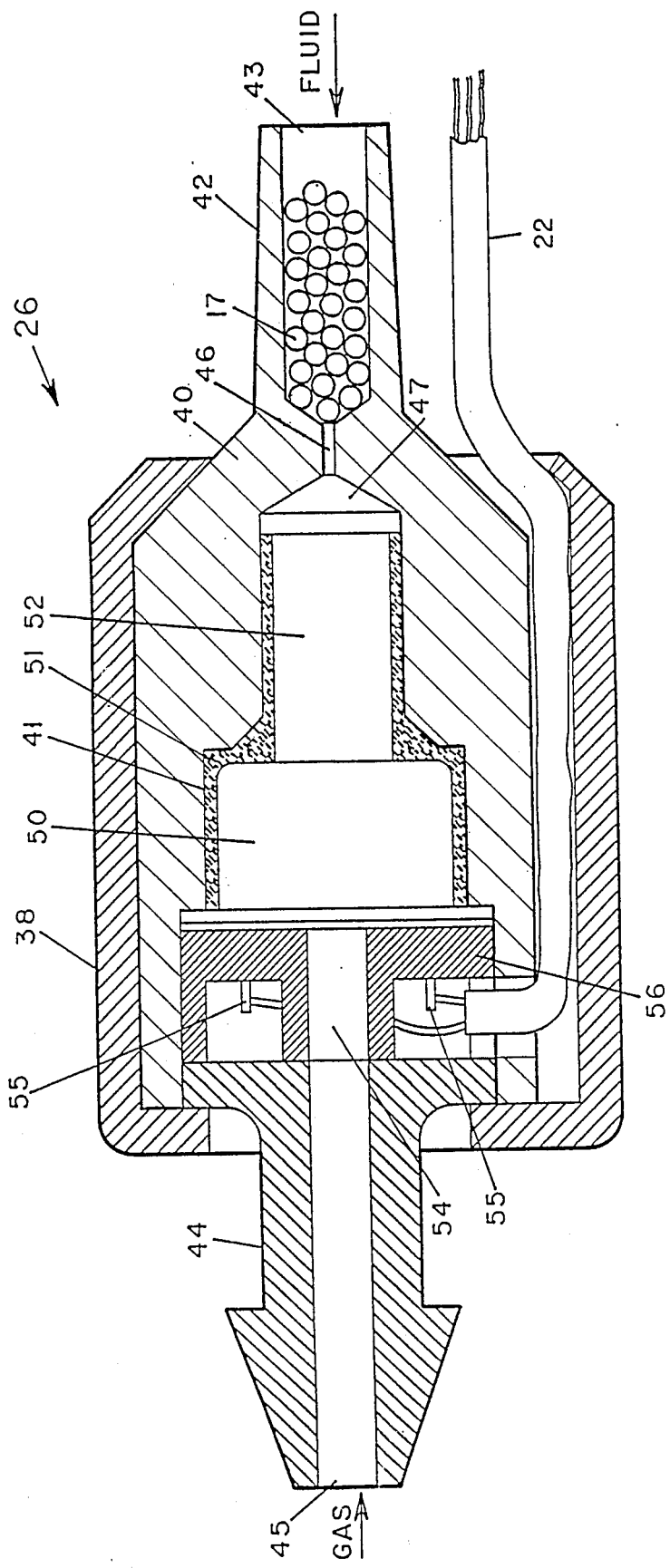
FIG. 5 is a cross-sectional side view of the sensor assembly taken along lines 5—5 of FIG. 3, showing details relating to the placement of the pressure transducer within the finger mounting bracket.

Details relating to the components used in the invention cuff position compensation system can be seen by referring to FIGS. 3 through 5. Referring to FIG. 3, the major system components can be seen to include a tube assembly 12, a sensor assembly 14 and a fluid reservoir chamber 16. The tube assembly 12 includes a flexible, fluid-filled tube 18, a pneumatic line 20 and an electronic signal line 22. The pneumatic line 20 is connected to an appropriate pump or supply of pressurized gas for inflating the occlusion cuff 28.

The sensor assembly 14 comprises a housing 24 which is adapted to receive the transducer assembly 26 (shown in phantom) and the occlusion cuff 28. Details relating to the housing 24 can be seen by referring to FIGS. 4a and 4b. The housing 24 comprises an elongated lower arcuate bracket 30 which is adapted to receive a patient's finger. The bracket 30 includes two lower curved gripping arms 32 and 33 which serve to secure the housing in surrounding relation to the patient's finger. The housing is further secured to the patient's finger by the occlusion cuff 28 which is received through longitudinal slots 34 in a U-shaped platform 36 attached to lower bracket 30, as shown in FIG. 4b. A generally tubular upper housing 38 is attached to the U-shaped platform 36. This upper housing comprises a cylindrical cavity 39 which is adapted to receive the transducer assembly 26 as shown in FIG. 5.

The occlusion cuff 28 is releasably secured to the patient's finger by a strip of thistle-type connectors 29 which are adapted to engage a felt-like covering on the outer surface of the cuff body 27. The occlusion cuff 28 is pressurized by a stream of gas provided by a pneumatic tube 23 which is connected to the connector 21 of pneumatic line 20. With the cuff 28 attached to the patient's finger and pressurized to an appropriate level, pressure variations in the underlying blood vessel will be translated to a pressure variation in the pressure of the gas in the cuff 28. This pressure variation is communicated to the differential pressure transducer in the sensor assembly 14, as described below.

The transducer assembly 26 includes a generally tubular body 40 which has an internal longitudinal cavity 41 adapted to receive the differential pressure transducer 50 and appropriate pneumatic fittings. The body 40 is tapered on one end to define a male fluid connector 42 which is adapted to receive a complementary female connector 19 attached to the fluid tube 18, shown in FIG. 3. Fluid from the tube 18 is communicated into the body 40 via longitudinal bore 43 in connector 42. A male pneumatic connector 44 is received in the cavity 41 on the opposite side of the body 40. The pneumatic connector 44 is adapted to receive the curved portion of the occlusion cuff pressurization tube 23' and to communicate gas pressure therefrom to the differential pressure transducer 50 via longitudinal bore 45.

The differential pressure transducer 50 is provided with a fluid pressure port 52 and a pneumatic pressure port 54 for sensing pressures provided by the fluid tube 18 and the pneumatic tube 23' of the occlusion cuff, respectively. As can be seen in FIG. 5, the pressure sensed by fluid port 52 will be equal to the pressure of the fluid in chamber 47 which is connected to the longitudinal bore by a constricted flow channel 46. The transducer provides an electrical output signal at terminals 55 corresponding to the difference between the pressures sensed at the respective pressure ports.

The transducer 50 is received in the cavity 41, as shown in FIG. 5, with a layer of polymer sealant 51 providing a fluid seal between the fluid port 54 and the inner surface of the cavity. The transducer is secured in the cavity by the layer of sealant 51 and by a retaining collar 56 which is received in surrounding relation to the pneumatic pressure port 54 of the transducer.

As was discussed above a portion of the fluid-filled tube 18 is filled with a plurality of silica sand particles 17 which serve as a low pass mechanical filter to prevent transient pressure signals from being communicated to the differential pressure transducer 50. With the fluid tube 18 connected to the fluid port 42, some of these particles will reside in the longitudinal bore 43 in connector 42, as shown in FIG. 5. The constricted flow channel of the preferred embodiment has an internal diameter of 0.0135, which is sufficiently small to prevent these particles from entering chamber 47. The particles 17 are retained in the desired position within the tube 18 by an additional retainer at the opposite end of the particle column.

The constricted flow channel 46 serves a dual purpose of retaining the silica sand particles 17, as described above, and of moderating the flow of fluid between chamber 47 and the longitudinal bore 43. The channel 46 thus serves as a second mechanical filter to remove transient pressure components from the hydrostatic pressure sensed by the fluid pressure port 52 of the transducer 50.

In addition to the mechanical filtering characteristics discussed above, the fluid reservoir 16 of the compensation system ensures accurate pressure readings by compensating for nonhydrostatic pressure differentials caused by factors such as movement of the tube and changes in the temperature of the fluid in the tube. Details relating to the fluid reservoir can be seen by referring to FIG. 3a. The reservoir comprises a fluid-filled compliant bag 60 which is contained in a semi-rigid housing 62. The housing comprises an adhesive backing 64 to allow it to be attached to a patient as shown in FIGS. 1a–1c. A vent 63 is provided in the upper surface of the housing 62 to equalize air pressure in the housing as the volume of the bag 60 changes. In the preferred embodiment, the compliant bag 60 is formed of polyethylene having a thickness of 1.5 mil. The compliant bag is infinitely compliant over the range of pressure and volume changes experienced in normal operation of the invention compensation system. In operation, it has been found that the compliant bag 60 should be capable of absorbing up to 25% of the total volume of fluid contained in the tube 18 to ensure accurate pressure readings.

In operation, the sensor assembly 14 is placed on the patient's finger with the appropriate fluid and pneumatic lines attached to the transducer assembly 26 and occlusion cuff 28, as shown in FIG. 3. The occlusion cuff is then placed through the longitudinal slots in the transducer housing 24 and is secured in surrounding relation to the patient's finger. With the cuff pressurized to an appropriate level, pressure variations in the blood vessel in the patient's finger will cause variations in the pressure of the gas in the cuff 28. These variations in the cuff pressure will be communicated via tube 23' to the pneumatic port 54 of the differential pressure transducer 50. As has been discussed above, this pressure will include a pressure component corresponding to the blood pressure in the patient's heart and a hydrostatic pressure component produced by the column of blood in the patient's blood vessel. An offsetting pressure corresponding to the hydrostatic pressure in the blood vessel is communicated to the fluid port 52 of the transducer 50. The transducer 50 provides an output signal corresponding to the difference in pressure between the two ports. This signal can be processed by appropriate computer algorithms to obtain an accurate indication of the patient's actual blood pressure.

The preferred embodiment of the invention compensation is based on the use of a single differential pressure transducer 50. It is possible, however, to achieve the desired pressure offset by using a compensation system comprising two separate pressure transducers. In such a system, one transducer would provide an output signal related to the pressure in the occlusion cuff attached to the patient's limb. The other transducer would provide a reading of the hydrostatic pressure in the fluid-filled tube. This latter pressure reading could then be subtracted from the first to obtain a pressure signal equal to the patient's actual blood pressure.

The transducer position compensation system of the present invention has been discussed in connection with blood pressure readings taken at a point below the level of the patient's heart. It is important to emphasize that the invention is not limited to this particular application, but can also be used to compensate for pressure differentials related to measurements made at positions above the level of the patient's heart.

While the invention method and apparatus for compensating for the transducer position in a blood pressure monitoring system has been described in connection with the preferred embodiment, it is not intended to be limited to the specific form set forth herein, but on the contrary, it is intended to cover such alternatives, modifications and equivalents as may be reasonably included within the spirit and scope of the invention as defined by the appended claims.

We claim:

1. In a blood pressure monitoring system, an apparatus for compensating for the position of a pressure transducer relative to the position of a patient's heart, comprising:
   means for sensing blood pressure in a blood vessel, said blood pressure comprising a first pressure component corresponding to the blood pressure in said patient's heart and a second pressure component corresponding to the hydrostatic pressure of the blood contained in said blood vessel;
   a pressure transducer having first and second pressure sensing ports, said transducer having means for comparing the relative magnitude of pressures sensed at said first and second ports and means for producing an output signal corresponding to the difference between the pressure sensed at said first and second ports;
   means for creating an offsetting pressure equal to said second pressure component;
   means for communicating said blood pressure sensed in said blood vessel to said first port of said pressure transducer; and
   means for communicating said offsetting pressure to said second port of said pressure transducer.

2. The apparatus according to claim 1, said means for sensing said blood pressure comprising an pressurizable occlusion cuff releasably secured in surrounding relation to a limb containing said blood vessel.

3. The apparatus according to claim 2, said means for creating said offsetting pressure comprising a column of fluid, said fluid having a density approximately equal to the density of the blood contained in said blood vessel.

4. The apparatus according to claim 3, said means for providing said offsetting pressure further comprising mechanical filter means for filtering transient pressure variations in said offsetting pressure.

5. The apparatus according to claim 4, said mechanical filtering means comprising a plurality of particles of silica sand contained in column of fluid.

6. The apparatus according to claim 5, said particles of silica sand having a diameter of approximately 0.025 inch.

7. The apparatus according to claim 6, further comprising a second means for filtering transient pressure variations from said offsetting pressure, said second filtering means comprising a constricted flow passage between said column of fluid and said second port of said pressure transducer.

8. The apparatus according to claim 7, said pressure comparing means comprising a differential pressure transducer providing an electrical output signal corresponding to the difference in pressures sensed at said first and second ports.

9. The apparatus according to claim 8, further comprising means for absorbing pressure variations associated with changes in the temperature of said fluid contained in said fluid column.

10. The apparatus according to claim 9, said means for absorbing said pressure variations comprising a compliant bag contained in a housing adopted to be attached to said patient at approximately the level of said patient's heart.

11. The apparatus according to claim 10, said compliant bag having sufficient capacity to absorb up to 25% of the fluid contained in said fluid column.

12. The apparatus according to claim 5, said mechanical filtering means comprising a plug of sintered metal contained in aid column of fluid.

13. An apparatus for compensating for the position of a pressure transducer relative to the position of a patient's heart, comprising:
   means for sensing blood pressure in a blood vessel, said blood pressure comprising a first pressure component corresponding to the pressure in said patient's heart and a second pressure component corresponding to the hydrostatic pressure of the blood contained in said blood vessel;
   a differential pressure transducer having first and second pressure sensing ports, said transducer including means for comparing the relative magnitude of pressure sensed at said first and second ports and means for producing an output signal corresponding to the difference between the pressure sensed at said first and second ports;
   a flexible tube containing a column of fluid for creating an offsetting pressure equal to said second pressure component, said fluid having a density approximately equal to the density of blood;
   means for communicating said blood pressure sensed in said blood vessel to said first port of said differential pressure transducer;

means for communicating said offsetting pressure to said second port of said differential pressure transducer;

means for filtering transient pressure components from said offsetting pressure created by said fluid contained in said fluid-fllled tubbe; and means for absorbing pressure variations caused by temperature variations of said fluid contained in said fluid filled tube.

14. The apparatus according to claim 13, said flltering means comprising a plurality of particles of silica sand contained in said flexible tube, said particles having a diameter of approximately 0.025 inch.

15. The apparatus according to claim 14, further comprising a second mechanical filtering means for filtering transient signals, said second filtering means comprising a constricted flow passage between said second port of said differential pressure transducer and said column of fluid for providing said offsetting pressure.

16. The apparatus according to claim 15, said means for absorbing said pressure variations of said fluid comprising a compliant bag having sufficient capacity to absorb up to 25% of the fluid contained in said tube, said compliant bag being contained in a housing at approximately the same level as the heart of said patient.

17. In a blood pressure monitoring system, a method for compensating for the position of a pressure sensor relative to the position of a patient's heart, comprising the steps of:

measuring the blood pressure in a blood vessel, said blood pressure comprising a first pressure component corresponding to the pressure in said patient's heart and a second pressure component corresponding to the hydrostatic pressure of the blood contained in the blood vessel;

creating an offsetting pressure corresponding to said second pressure component subtracting said offsetting pressure component from said blood pressure measured in said blood vessel; and providing an output signal corresponding to the pressure in said patient's heart.

18. The method according to claim 17, further comprising the step of filtering transient pressure variations in said offsetting pressure.

19. The method according to claim 18, said offsetting pressure being created by a column of fluid, said fluid having a density approximately equal to the density of blood.

20. The method according to claim 19, said step of flltering said pressure variations from said offsetting pressure comprising the step of passing said column of fluid through a mechanical filter comprising a plurality of particles of silica sand.

* * * * *